[12] United States Patent  
Murata et al.

(10) Patent No.: US 7,683,199 B2  
(45) Date of Patent: Mar. 23, 2010

(54) FLUORINE-CONTAINING POLYETHER PHOSPHONIC ACID ESTER COMPOUND AND PROCESS FOR PRODUCING THE SAME

(75) Inventors: Seiichiro Murata, Kitaibaraki (JP); Hideki Abe, Kitaibaraki (JP); Keisuke Kokin, Kitaibaraki (JP)

(73) Assignee: Unimatec Co., Ltd., Tokyo (JP)

( * ) Notice: Subject to any disclaimer, the term of this patent is extended or adjusted under 35 U.S.C. 154(b) by 127 days.

(21) Appl. No.: 11/791,310

(22) PCT Filed: Nov. 24, 2005

(86) PCT No.: PCT/JP2005/021525

§ 371 (c)(1),
(2), (4) Date: May 21, 2007

(87) PCT Pub. No.: WO2006/057272

PCT Pub. Date: Jun. 1, 2006

(65) Prior Publication Data

US 2008/0114184 A1    May 15, 2008

(30) Foreign Application Priority Data

Nov. 25, 2004 (JP) ............................. 2004-339858

(51) Int. Cl.
*C07F 9/02* (2006.01)
(52) U.S. Cl. ..................................... 558/161
(58) Field of Classification Search ............. 558/161
See application file for complete search history.

(56) References Cited

U.S. PATENT DOCUMENTS 3,989,772 A    11/1976   Hendricks et al.

FOREIGN PATENT DOCUMENTS

| JP | 58-180598 | 10/1983 |
| JP | 59 066496 | 4/1984 |
| JP | 61-254697 | 11/1986 |
| JP | 09-202793 | 8/1997 |
| JP | 2002-069037 | 3/2002 |
| JP | 2003-176831 | 6/2003 |

OTHER PUBLICATIONS

Chen et al. Perfluoroalkylations and Perfluorooxaalkylations. Part 2. Copper-Mediated Cross-coupling of Secondary Perfluorooxaalkyl Iodides and Aryl Halides. J. or Fluorine Chemistry 65 (1993) 59-63.

*Primary Examiner*—Rei-tsang Shiao  
(74) *Attorney, Agent, or Firm*—Brinks Hofer Gilson & Lione

(57) ABSTRACT

A fluorine-containing polyether phosphonic acid ester compound represented by the following general formula:

$(R_2O)(R_1O)P(O)(CH_2)_aCF(CF_3)[OCF_2CF(CF_3)]_bO$
$(CF_2)_cO[CF(CF_3)CF_2O]_dCF(CF_3)(CH_2)_eP(O)$
$(OR_3)(OR_4)$ (where $R_1$, $R_2$, $R_3$ and $R_4$ are hydrogen atoms, alkyl groups, cycloalkyl groups, aryl groups, alkylaryl groups, aralkyl groups, or any of the foregoing groups substituted with halogen atoms, and subscripts a, b, c, d, and e are in conditions of $2 \leq a+e \leq 8$, $b+d \leq 28$, and $1 \leq c \leq 10$, and subscripts b and d may be 0). The fluorine-containing polyether phosphonic acid ester compound is produced by reaction of a fluorine-containing polyether dialkyl halide represented by the following general formula:

$X(CH_2)_aCF(CF_3)[OCF_2CF(CF_3)]_bO(CF_2)_cO[CF(CF_3)CF_2O]_dCF(CF_3)(CH_2)_eX$ (X: Cl, Br or I)
with a phosphite compound represented by the following general formula:

$(R_1O)(R_2O)P(OR)$ and/or $(R_3O)(R_4O)P(OR)$ (R: a hydrogen atom or a lower alkyl group).

4 Claims, No Drawings

FLUORINE-CONTAINING POLYETHER PHOSPHONIC ACID ESTER COMPOUND AND PROCESS FOR PRODUCING THE SAME

TECHNICAL FIELD

The present invention relates to a novel fluorine-containing polyether phosphonic acid ester compound and a process for producing the same, and more particularly to a novel fluorine-containing polyether phosphonic acid ester compound having phosphonic acid ester groups at both terminals, and a process for producing the same.

BACKGROUND ART

Fluorine-containing polyether phosphonic acid esters are widely used as a resin antioxidant, an anti-freezing liquid, an antistatic agent for fibers, a flame retardant for fiber, a surfactant, a mold release agent, etc.

So far proposed fluorine-containing polyether phosphonic acid esters have a phosphonic acid ester only at one terminal of the respective molecules, and no compounds having phosphonic acid esters at both terminals have been known yet.

Patent Literature 1: JP-B-2-45571

DISCLOSURE OF THE INVENTION

PROBLEM TO BE SOLVED BY THE INVENTION

An object of the present invention is to provide a novel fluorine-containing polyether compound having phosphonic acid ester groups at both terminals, and a process for producing the same.

MEANS FOR SOLVING THE PROBLEM

The present invention provides a fluorine-containing polyether phosphonic acid ester compound represented by the following general formula:

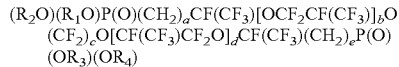

(where $R_1$, $R_2$, $R_3$ and $R_4$ are hydrogen atoms, alkyl groups, cycloalkyl groups, aryl groups, alkylaryl groups, aralkyl groups, or any of the foregoing groups, some or whole of whose hydrogen atoms are substituted with halogen atoms, and subscripts a, b, c, d, and e are integers satisfying the conditions of $2 \leq a+e \leq 8$, $b+d \leq 28$, and $1 \leq c \leq 10$, and the subscripts b and d may be 0).

Such a fluorine-containing polyether phosphonic acid ester compound can be produced by reaction of a fluorine-containing polyether dialkyl halide represented by the following general formula:

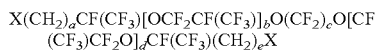

(where X is Cl, Br or I, and subscripts a, b, c, d, and e have the same meanings as defined above) with a phosphite compound represented by the following general formula:

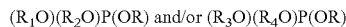

(where R is a hydrogen atom or a lower alkyl group having 1-4 carbon atoms, and $R_1$, $R_2$, $R_3$ and $R_4$ have the same meanings as defined above).

EFFECT OF THE INVENTION

The present invention provides a novel fluorine-containing polyether compound having phosphonic acid ester groups at both terminals. The novel fluorine-containing polyether phosphonic acid ester compound can be effectively used as a resin antioxidant, an anti-freezing liquid additive, an antistatic agent for fibers, or a flame retardant for fiber, a surfactant, a mold release agent, etc.

BEST MODES FOR CARRYING OUT THE INVENTION

The present novel fluorine-containing polyether phosphonic acid ester compound can be produced by reaction of a fluorine-containing polyether dialkyl halide represented by the following general formula:

where X: Cl, Br, or I with one kind or two kinds of phosphonic acid or phosphonic acid ester (phosphite compound), preferably trialkyl phosphite, represented by the following general formulae:

 [A]

 [B]

where R: a hydrogen atom or a lower alkyl group, and $R_1$, $R_2$, $R_3$ and $R_4$: as defined above In the case of using one kind of the same phosphite compound [A] or [B], diphosphonic acid ester compound with the same both terminal groups can be obtained, whereas in the case of using mutually different phosphite compounds [A] and [B], a mixture of a diphosphonic acid ester compound having different two terminal group and the compound having the same both terminal groups can be obtained.

The fluorine-containing polyether dialkyl halide as a raw material can be obtained from fluorine-containing polyether dicarboxylic acid halide represented by the following general formula as a starting material:

That is, among the fluorine-containing polyether dialkyl halides, fluorine-containing polyether dialkyl iodide can be obtained by reaction of said fluorine-containing polyether dicarboxylic acid fluoride (X=F) with lithium iodide, followed by ultraviolet ray irradiation, or by portion-by-portion addition of fluorine-containing polyether dicarboxylic acid fluoride to an iodine/diglyme solution containing cesium carbonate, thereby producing

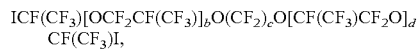

followed by reaction with ethylene, thereby producing

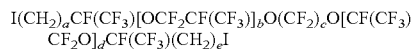

The corresponding dialkyl halide of X=Cl or Br can be produced by halogen exchange method.

Patent Literature 2: JP-A-4-103553

Non-patent Literature 1: J. Fluorine Chem. 65, pp 59-65 (1993)

Why the condition of $2 \leq a+e \leq 8$ is herein set forth in the fluorine-containing polyether phosphonic acid ester compound is due to easiness of synthesis, why the condition of b+d≦28 is herein set forth is due to the fact that the aforementioned fluorine-containing polyether dicarboxylic acid fluoride to be used as the starting material has an integer of 0 or not more than 28 as disclosed for b+d in the following Patent Literature 3, and why the condition of 1≦c≦10, preferably 2≦c≦10, is herein set forth is due to the fact that the Patent Literature 3 discloses an integer of 2 or more for c. The subscript c value of 2-6 is more preferable due to easy availability of the raw material, and the subscripts b+d value of not more than 20 is more preferable due to easy production.

Patent Literature 3: JP-A-2002-69037

Preferable phosphite compound for use in the reaction with such a fluorine-containing polyether dialkyl halide includes, for example, trialkyl phosphites such as trimethyl phosphite, triethyl phosphite, tripropyl phosphite, tributyl phosphite, etc. In addition, tricyclohexyl phosphite, triphenyl phosphite, tritolyl phosphite, etc. can be used.

In the reaction, it is preferable to make portion-by-portion addition of phosphite compound to prevent considerable consumption thereof due to the reaction with by-products.

The reaction temperature is not particularly limited, so long as it is 100° C. to not higher than the boiling point of phosphite compound. However, the reaction time is prolonged at lower temperatures, whereas by-products are much produced at higher temperatures. Thus, preferable reaction temperature is 120°-130° C.

The fluorine-containing polyether diphosphonic acid ester compounds so synthesized include, for example, the following compounds. For the alkyl groups, cycloalkyl groups, alkylaryl groups and aralkyl groups of $R_1$, $R_2$, $R_3$ and $R_4$, usually alkyl groups having 1-10 carbon atoms are used.

$(C_2H_5O)_2P(O)(CH_2)_2CF(CF_3)OCF_2CF(CF_3)O(CF_2)_2$
$OCF(CF_3)CF_2OCF(CF_3)(CH_2)_2P(O)(OC_2H_5)_2$ $(C_3H_7O)_2P(O)(CH_2)_aCF(CF_3)[OCF_2CF(CF_3)]_bO$
$(CF_2)_4O[CF(CF_3)CF_2O]_dCF(CF_3)(CH_2)_eP(O)$
$(OC_3H_7)_2$

2≦a+e≦6 and 2≦b+d≦6

$(C_3H_7O)_2P(O)(CH_2)_2CF(CF_3)[OCF_2CF(CF_3)]_bO$
$(CF_2)_6O[CF(CF_3)CF_2O]_dCF(CF_3)(CH_2)_2P(O)$
$(OC_3F_7)_2$

10≦b+d≦16

$(C_3H_7O)(HO)P(O)(CH_2)_aCF(CF_3)[OCF_2CF(CF_3)]_bO$
$(CF_2)_4O[CF(CF_3)CF_2O]_dCF(CF_3)(CH_2)_eP(O)$
$(OH)(OC_3H_7)$

2≦a+e≦6 and 2≦b+d≦6

$(HO)_2P(O)(CH_2)_aCF(CF_3)[OCF_2CF(CF_3)]_bO(CF_2)_4O$
$[CF(CF_3)CF_2O]_dCF(CF_3)(CH_2)_eP(O)(OH)_2$

2≦a+e≦6 and 2≦b+d≦6

$(C_6H_{11}O)_2P(O)(CH_2)_2CF(CF_3)OCF_2CF(CF_3)O$
$(CF_2)_2OCF(CF_3)CF_2OCF(CF_3)(CH_2)_2P(O)$
$(OC_6H_{11})_2$ $(C_6H_{11})_2P(O)(CH_2)_2CF(CF_3)OCF_2CF(CF_3)O(CF_2)_2$
$OCF(CF_3)CF_2OCF(CF_3)(CH_2)_2P(O)$
$(OC_6H_4CH_3)_2$ $(CH_3C_6H_4O)_2P(O)(CH_2)_2CF(CF_3)OCF_2CF(CF_3)O$
$(CF_2)_2OCF(CF_3)CF_2OCF(CF_3)(CH_2)_2P(O)$
$(OC_6H_4CH_3)_2$ $(C_6H_5O)_2P(O)(CH_2)_2CF(CF_3)[OCF_2CF(CF_3)]_2O$
$(CF_2)_2O[CF(CF_3)CF_2O]_2CF(CF_3)(CH_2)_2P(O)$
$(OC_6H_5)_2$ $(C_6H_5O)_2P(O)(CH_2)_2CF(CF_3)[OCF_2CF(CF_3)]_2O$
$(CF_2)_2O[CF(CF_3)CF_2O]_2CF(CF_3)(CH_2)_2P(O)$
$(OH)(OC_6H_5)$

EXAMPLES

The present invention will be described in detail below, referring to Examples.

Example 1

101 g (110 m moles) of fluorine-containing polyether diiodide (99 GC %) represented by the following formula:

$ICF(CF_3)OCF_2CF(CF_3)O(CF_2)_2OCF(CF_3)CF_2OCF(CF_3)I$ and 1.2 g (8.2 m moles) of t-butyl peroxide were charged into an autoclave having a capacity of 200 ml, and after the reactor vessel inside was thoroughly degasified, the reactor was heated with stirring. When the inside temperature reached to 105° C., ethylene was introduced thereto to make the inside pressure 0.4 MPa. While the inside temperature was kept at 115° C., ethylene was repeatedly introduced thereto to keep that inside pressure and conduct ageing for one hour, whereby 107 g of fluorine-containing polyether diethyl iodide (97 GC %), represented by the following formula, was obtained (yield 97%):

$I(CH_2)_2CF(CF_3)OCF_2CF(CF_3)O(CF_2)_2OCF(CF_3)CF_2OCF(CF_3)(CH_2)_2I$ 24.9 g (24.8 m moles) of the resulting fluorine-containing polyether diethyl iodide was charged into a flask having a capacity of 200 ml, provided with a condenser, a thermometer, and a gas flushing capillary, and 52.3 g (315 m moles) of triethyl phosphite $(C_2H_5O)_3P$ was added thereto portion-by-portion, while flushing a nitrogen gas thereto. Stirring was conducted at 130° C. for 80 hours. The reaction product was washed with city water, an aqueous saturated sodium hydrogen carbonate solution, and an aqueous saturated sodium chloride solution in this order, and the organic layer was dried over magnesium sulfate anhydride, whereby 21.1 g of the desired colorless, transparent, highly viscous liquid at the ordinary temperature, represented by the following formula was obtained (75 GC %, yield: 64.1%):

$(C_2H_5O)_2(O)P—(CH_2)_2CF(CF_3)OCF_2CF(CF_3)O$
$(CF_2)_2OCF(CF_3)CF_2OCF(CF_3)(CH_2)_2—P(O)$
$(OC_2H_5)_2$

It was confirmed by the following determination by $^1$H-NMR and $^{19}$F-NMR that the resulting compound was a desired compound given by the foregoing formula.

$^1$H-NMR(CDCl$_3$, TMS); δ 1.25 (CH$_3$), 1.84 (CF(CF$_3$) CH$_2$), 2.37 (CH$_2$P), 4.05 (OCH$_2$)

$^{19}$F-NMR(CDCl$_3$, CFCl$_3$); ppm-145.93 (OCE), −130.84 (CFCH$_2$), −87.01 (CF(CF$_3$)CF$_2$), −83.82 (CF(CF$_3$)CH$_2$), −82.19 (OCF$_2$CF$_2$O), −80.87 (CF(CF$_3$)CF$_2$), By simple distillation of the foregoing highly viscous liquid in a miniature simple distiller under conditions of inside pressure: 0.2 kPa, outside temperature: 189° C., and column top temperature: max. 132° C., 16.7 g of desired product (purity: 93 GC %) was obtained (distillation yield 98.1%).

Example 2

25.0 g (24.9 m moles) of fluorine-containing polyether diethyl iodide (97GC %) prepared in Example 1 was charged into a flask having a capacity of 200 ml, provided with a condenser, a thermometer, stirring blades and a gas flushing capillary, and heated to an inside temperature of 130° C. with stirring, while flushing a nitrogen gas thereto. Then, 65.6 g (315 m moles) of tri(isopropyl) phosphite [(CH$_3$)$_2$CHO]$_3$P was slowly added thereto portion-by-portion, followed by stirring at 130° C. for 96 hours. The reaction product was washed with city water, an aqueous saturated sodium hydrogen carbonate solution, and an aqueous sodium chloride solution in this order, and the organic layer was dried over magnesium sulfate anhydride whereby 23.8 g of the desired colorless, transparent, highly viscous liquid at the ordinary temperature (68 GC %) represented by the following formula, was obtained (yield: 62%):

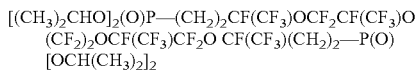

It was confirmed by the following determination by $^1$H-NMR and $^{19}$F-NMR that the resulting compound was a desired compound given by the foregoing formula.

$^1$H-NMR(CDCl$_3$, TMS); δ 1.27(CH$_3$), 2.38(CH$_2$P), 2.40(CF(CF$_3$)CH$_2$), 4.00(CHO)

$^{19}$F-NMR(CDCl$_3$, CFCl$_3$); ppm-145.90 (OCF), −130.82 (CFCH$_2$), −87.05 (OCF(CF$_3$)CF$_3$), −83.88 (CF(CF$_3$)CH$_2$), −82.17 (OCF$_2$CF$_2$), −80.83 (OCF(CE$_3$)CF$_2$), By simple distillation of the foregoing highly viscous liquid in a miniature simple distiller under the conditions of inside pressure: 0.2 kPa, outside temperature: 200° C., and column top temperature: max. 145° C., the low boiling fractions were removed, whereby 16.6 g of desired compound (purity: 95 GC %) was obtained (distillation yield: 97%).

Example 3

10 g (90.4 m moles) of fluorine-containing polyether diiodide (98 GC %), represented by the following formula:

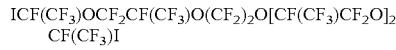

and 1.0 g (6.84 m moles) of di-t-butyl peroxide were charged into an autoclave having a capacity of 200 ml, and after the reactor vessel inside was thoroughly degasified, heated with stirring. When the inside temperature reached to 105° C., ethylene was introduced thereto to make the inside pressure 0.4 MPa. When the inside pressure was reduced to 0.1 MPa, ethylene was introduced thereto again and repeatedly to make 0.4 MPa, while keeping the inside temperature at 115° C. Introduction of ethylene was continued until the inside pressure was no more lowered.

Then, heating and stirring were continued at 115° C. for one hour, and 104.1 g of fluorine-containing polyether diethyl iodide (96 GC %), represented by the following formula, was obtained (yield: 97%).

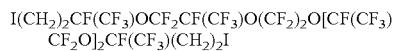

30.0 g (25.3 m moles) of the fluorine-containing polyether diethyl iodide was charged into a flask having a capacity of 200 ml, provided with a condenser, a thermometer, stirring blades and a gas flushing capillary, and heated to an inside temperature of 130° C. with stirring, while flushing a nitrogen gas thereto. Then, 53.4 g (321 m mole) of triethyl phosphite (C$_2$H$_5$O)$_3$P was slowly added thereto portion-by-portion, followed by stirring at 130° C. for 96 hours. The reaction product was washed with city water, an aqueous saturated sodium hydrogen carbonate solution, and an aqueous saturated sodium chloride solution in this order. The organic layer was dried over magnesium sulfate anhydride, whereby 27.7 g of desired, colorless, transparent, highly viscous liquid at the ordinary temperature (69 GC %), given by the following formula, was obtained (yield 65%).

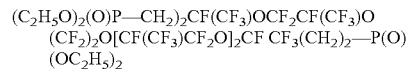

It was confirmed by the following determination by $^1$H-NMR and $^{19}$F-NMR that the resulting compound was a desired compound given by the foregoing formula.

$^1$H-NMR(CDCl$_3$, TMS); δ 1.27 (CH$_3$), 1.85 (CF(CF$_3$) CH$_2$) 2.39 (CH$_2$P), 4.10 (OCH$_2$)

$^{19}$F-NMR(CDCl$_3$, CFCl$_3$); ppm-145.89 (OCF), −130.83 (CFCH$_2$), −87.00 (CF(CF$_3$)CF$_2$), −83.84 (CF(CF$_3$)CH$_2$), −82.17 (OCF$_2$CF$_2$O), −80.85 (CF(CF$_3$)CF$_2$), By simple distillation of the foregoing highly viscous liquid in a miniature simple distiller under conditions of inside pressure: 0.2 kPa, outside temperature: 200° C., and column top temperature: max. 135° C., 19.5 g of desired compound (purity: 98 GC %) was obtained (distillation yield: 98%).

The invention claimed is:

1. A fluorine-containing polyether phosphonic acid ester compound, represented by the following general formula:

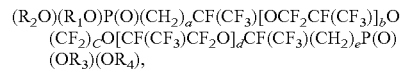

where R$_1$, R$_2$, R$_3$ and R$_4$ are hydrogen atoms, alkyl groups, cycloalkyl groups, aryl groups, alkylaryl groups, aralkyl groups or any of the foregoing groups, some or whole of whose hydrogen atoms are substituted with halogen atoms, and subscripts a, b, c, d, and e are integers satisfying conditions of 2≦a+e≦8, b+d≦28 and 1≦c≦10, and the subscripts b and d may be 0).

2. A fluorine-containing polyether phosphonic acid ester compound according to claim 1, wherein the subscript c of the general formula is an integer satisfying a condition of 2≦c≦10.

3. A fluorine-containing polyether phosphonic acid ester compound represented by the following formula:

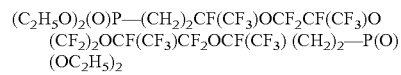

4. A process for producing a fluorine-containing polyether phosphonic acid ester compound according to claim 1, characterized by allowing a fluorine-containing polyether dialkyl halide represented by the following general formula:

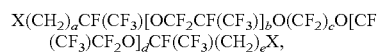

where X is Cl, Br or I, and a, b, c, d, and e are integers satisfying conditions of 2≦a+e≦8, b+d≦28, and 1≦c≦10, and the subscripts b and d may be 0), to react with a phosphite compound represented by the following general formula:

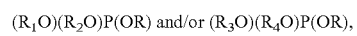

where R is a hydrogen atom, or a lower alkyl group having 1-4 carbon atoms, and R$_1$, R$_2$, R$_3$ and R$_4$ are hydrogen atoms, alkyl groups, cycloalkyl groups, aryl groups, alkylaryl groups, aralkyl groups or any of the foregoing groups, some or whole of whose hydrogen atoms are substituted with halogen atoms).

* * * * *